United States Patent [19]

Kelly et al.

[11] 4,293,379
[45] Oct. 6, 1981

[54] NEUTRON ACTIVATION ANALYSIS METHOD AND APPARATUS FOR DETERMINING SODIUM AND SODIUM COMPOUNDS IN LIQUID SAMPLES

[75] Inventors: Kerry J. Kelly, Midland, Mich.; Arthur J. Kamp, Oakley, Calif.

[73] Assignee: The Dow Chemical Company, Midland, Mich.

[21] Appl. No.: 134,046

[22] Filed: Mar. 26, 1980

[51] Int. Cl.³ .......................................... G01N 23/222
[52] U.S. Cl. .................................. 376/159; 23/230.3; 422/68
[58] Field of Search .......................... 23/230.3, 230 R; 422/71, 68; 250/432 R, 499, 500; 176/10

[56] References Cited
U.S. PATENT DOCUMENTS 3,461,291 8/1969 Goodman ...................... 250/500 X
3,781,556 12/1973 Taylor et al. ...................... 176/10 X
4,225,316 9/1980 Lewin ................................. 23/230.3

OTHER PUBLICATIONS

Anders, "Activation Analysis for Plant Stream Monitoring", Nucleonics, vol. 20, No. 2, Feb. 1962, pp. 78-83.
Anders, "Instrum. for Act. Anal. for Plant Instrum.", Pub. of the Inst. Soc. of Amer., Preprint No. 103--LA-61, Fall Conf. and Exhibit, L.A., Cal., Sep. 11-15, 1961.
Morgan et al., "Proced. of the N.A.T.O. Advanced Study Institute-Activation Analysis in Geochem. and Cosmochem.", Kjeller, Norway, Sep. 7-12, 1970, Universitetsforlagst, Oslo, 1971.

Primary Examiner—Ronald Serwin

[57] ABSTRACT

Sodium is determined, virtually without known interferences, based on neutron activation of liquid sample to produce radioactive $^{23}$Ne activation product from $^{23}$Na, sparging of the sample whereby a headspace gas mixture comprising $^{23}$Ne in an inert sparging gas is collected, and remote analysis of the headspace gas mixture to determine total parent sodium based on monitoring radiation emissions of $^{23}$Ne. As an illustration of utility, the analysis is demonstrated as applicable to determinations of sodium in aqueous or organic matrices at concentrations of 1 part per thousand and greater using preferred forms of $^{241}$Am/Be radioactive isotope as the activation source.

20 Claims, 7 Drawing Figures

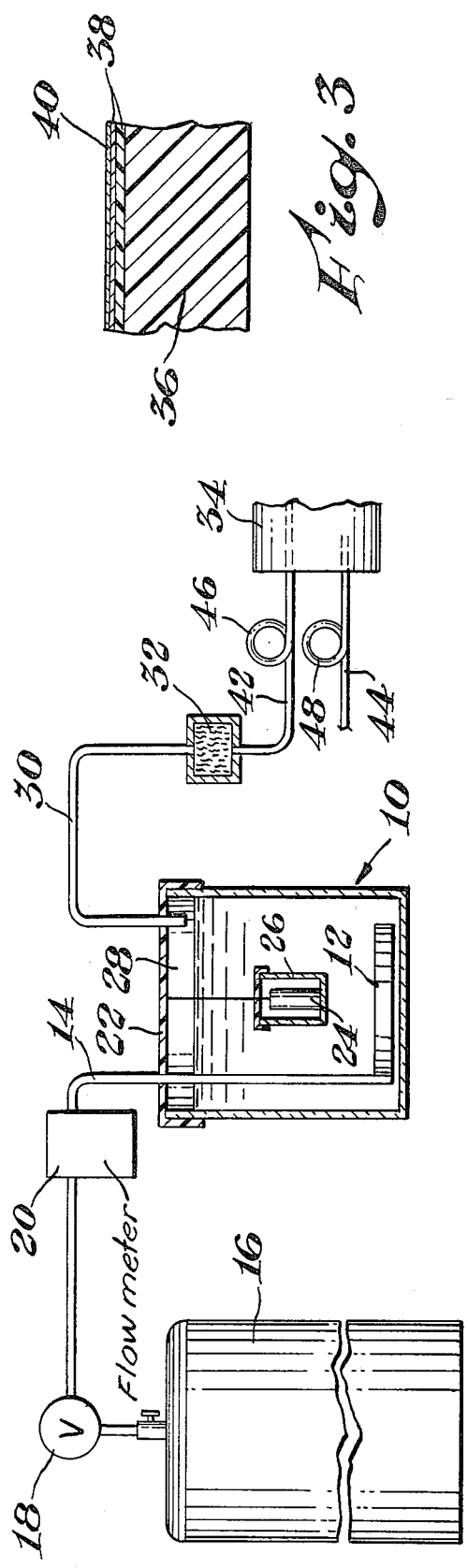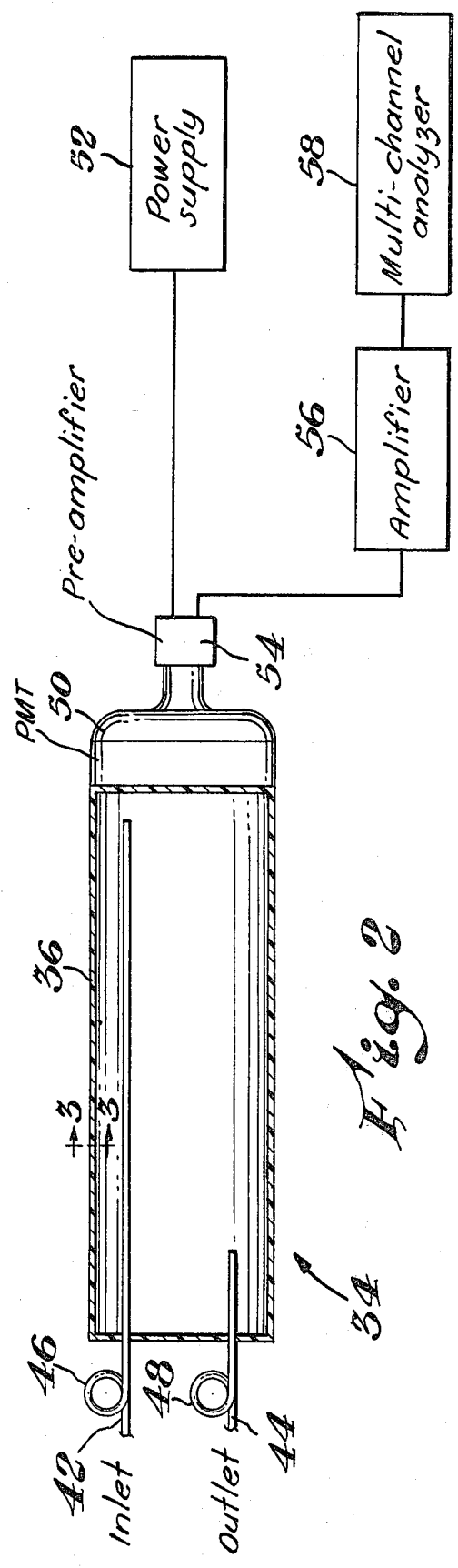

NEUTRON ACTIVATION ANALYSIS METHOD AND APPARATUS FOR DETERMINING SODIUM AND SODIUM COMPOUNDS IN LIQUID SAMPLES

FIELD OF THE INVENTION

The invention relates to the field of neutron activation analysis involving the interaction of sample nuclei with neutrons to produce short-lived radioactive activation products which can be detected by monitoring the radiation emitted. More particularly, the invention resides in improved method and apparatus for determining total sodium in liquid samples using neutron activation principles.

BACKGROUND OF THE INVENTION

Techniques currently used for on-line sodium analysis are known to have objectionable limitations in respect to the scope of applications possible. Ion selective electrodes, for example, tend to drift, require sample treatment, are affected by several difficult interferences, and are useful generally only when analyzing aqueous process streams or sample matrices. Conductivity methods are not selective and can be used only in specific cases. Accordingly, an improved analyzer for determining sodium on-line, and which would have general purpose utility, is particularly desired for process control applications.

PRIOR ART

Neutron activation analysis for sodium, based on gamma detection, is suggested within a broad process description by Anders, "Activation Analysis for Plant Stream Monitoring", Nucleonics, Vol. 20, No. 2, pp. 78–83 (Feb. 1962). Among the various elements said to be determinable by the described method is sodium by producing the activation product $^{23}$Ne gas having a half life of 38 seconds (stated by other sources to be 37 seconds). The technique called "activation analysis" is distinguished from the present invention in that there is no valid means of separation of the activation product from the sample mixture. It would, thus, be anticipated that the method would suffer from several strong interferences, and, further, any attempt to measure beta, as opposed to gamma, would be unsatisfactory because of strong beta absorption. Prior activation techniques based on monitoring beta, for example, have been characterized for reasons of strong beta absorption, as "practically restricted to trace analysis with reactor fluxes followed by chemical purification" (see Anders, "Instrumentation for Activation Analysis and Activation Analysis for Plant Instrumentation", publication of the Instrument Society of America, Conference Preprint No. 103-LA-61, Fall Instrument—Automation Conference and Exhibit, Los Angeles, California, Sept. 11–15, 1961).

Accordingly, prior techniques for monitoring sodium on-line by neutron activation are considered less than satisfactory and rarely, if ever, are implemented.

THE INVENTION

The improved analytical method of the invention for determining total sodium comprises exposing sodium containing liquid sample to a neutron flux effective to produce $^{23}$Ne radioactive gas activation product, sparging the liquid sample effective to evolve and separate from the sample a detectable concentration of $^{23}$Ne admixed with sparging gas, flow removing said evolved gas mixture to a space remote from the neutron flux emission, monitoring said removed gas mixture for radiation emission, and quantifying, based on radiation count, total sodium of the analyzed sample.

A further aspect of the invention is the improved analytical apparatus for neutron activation analysis comprising an activation cell, an activation source for producing a neutron flux within said activation cell, means to place sample within said activation cell, means to sparge said liquid sample, a headspace being defined for receiving sparging gas in admixture with gas sparged thereby which is solved from the liquid sample, a radiation detector remote from said activation cell, means shielding the radiation detector from neutron flux emission and background radiation emission, communication means for routing flow of the headspace gas mixture to the radiation detector to detect radiation emission of said gas mixture.

Activation sources of greater than about 3.6 MeV (meaning average energy whenever used herein) and preferably about 3.6–5.5 MeV are most ideally suited for use in practicing the invention. For reasons of minimizing shielding requirements and still obtaining adequate flux intensities, it is preferred that the activation source is between about 0.1–50 curies (Ci), and most preferably between about 0.5–15 Ci. Activation sources outside these limits may be successfully used, however. Generally above 6 MeV, there is some, but not a great difference in increased sensitivity to be gained, and these high energy sources can produce certain interferences. Such interferences, however, are not difficult, as discussed further below.

Specific activation sources available for the practice of the invention include 4–14 MeV generators, e.g., described by Morgan and Ehmann, Proceedings of the N.A.T.O. Advanced Study Institute—Activation Analysis in Geochemistry and Cosmochemistry, Kjeller, Sept. 7–12, 1970, Universitetsforlaget, Oslo, Norway, 1971, and herein incorporated fully by reference.

On-line analyzers would most preferably use as the activation source, a radioactive isotope immersed with the liquid sample. The best commercially available isotope is $^{241}$AM/Be (MeV 4.4). In addition, available $^{210}$Po/Be or $^{252}$Cf radioactive isotopes (MeV 2 and 1.5, respectively) would conceivably be useful to determine relatively high sodium concentrations, but have insufficient MeV values to be satisfactory other than for limited use.

As an illustration of relative sensitivities depending on activation source differences, sodium concentrations of greater than about 0.1 percent (1 part per thousand) are herein demonstrably achieved using, as the activation source, a 4.44 Ci, 4.4 MeV, $^{241}$Am/Be isotope. A sensitivity gain of several fold (i.e., 15/4.4) is possible using a 15 Ci $^{241}$Am/Be source. By replacing the $^{241}$Am/Be source with a 14 MeV neutron generator, with comparable neutron output or flux density, sensitivity can be increased to approximately the parts per million (ppm) or trace level, thus achieving roughly a five hundred fold sensitivity gain. A 0.5–15 Ci $^{241}$Am/Be source is preferred because it provides combined advantages of low initial costs, little maintenance, no half-life correction, no known interferences, relatively lower shielding requirements, and relatively good, although not the optimum, sensitivity.

In addition, sensitivity may be enhanced by operational and design factors such as optimizing sample size, sparging efficiency, and optimizing residence time of the headspace gas mixture within the counting chamber of the detector. It is possible, for example, to internally baffle, or otherwise beneficially modify, the counting chamber to extend the length of the flow path and thus the time of residence of the headspace gas in the counting chamber. The total radiation count is thus maximized to enhance the sensitivity level of the apparatus.

Sparging efficiency may be increased by increasing the rate of flow of sparging gas into the liquid sample. Eventually, however, the sensitivity level may be found to actually decrease, with increases in the rate of flow of the sparging gas due to correspondingly shorter residence time of the headspace gas in the detector and resulting lower count tabulations. Accordingly, an optimum flow rate is computed at that rate which produces the highest radiation count. This value defines optimum flow rate and is readily determinable empirically for any given apparatus design.

Since $^{23}$Ne beta emission (4.4, 4.0 MeV) is more intense than gamma, beta monitors are preferably employed in the design of the apparatus for optimizing count and thus sensitivity. Obviously, gamma may be monitored in conjunction or alternatively monitored. The preferred beta detector comprises a plastic or liquid scintillator, it being known that other detectors, such as a sodium iodide crystal scintillator, proportional counter, or ionization chamber may be used to monitor beta emission. Gamma detectors useful in practice of the invention would most preferably comprise a sodium iodide crystal scintillator or Ge(Li) detector. A highly efficient beta detector in structure is a flow-through hollow plastic scintillator, e.g., cylinder into which the headspace gas mixture flows and is ultimately expelled. Alternate detector structures known in the art may be effectively substituted or required, e.g., depending on the detector type.

The selection of the sparging gas is not generally critical since the noble gas $^{23}$Ne activation product is not highly reactive. The preferred sparging gas is thus a gas free of sodium contamination, a minimal beta absorber, and preferably, nonreactive with constituents in the sample. Air and nitrogen are the most preferred forms of sparging gas used in the practice of the invention.

In reference now to the following detailed description of specific embodiments of the invention, reference is also taken to the accompanying drawing wherein:

FIG. 1 is an elevational view showing the activation cell and sparging gas assemblage useful for neutron activation analysis according to the principles of the invention;

FIG. 2 is a view like FIG. 1 showing a preferred radiation detector and electronics for producing a usable visual readout of the counting results of the radiation detector;

FIG. 3 is a greatly enlarged cross-sectional view taken along reference line 3—3 of FIG. 2.

DETAILED DESCRIPTION OF THE INVENTION

Figure 4:
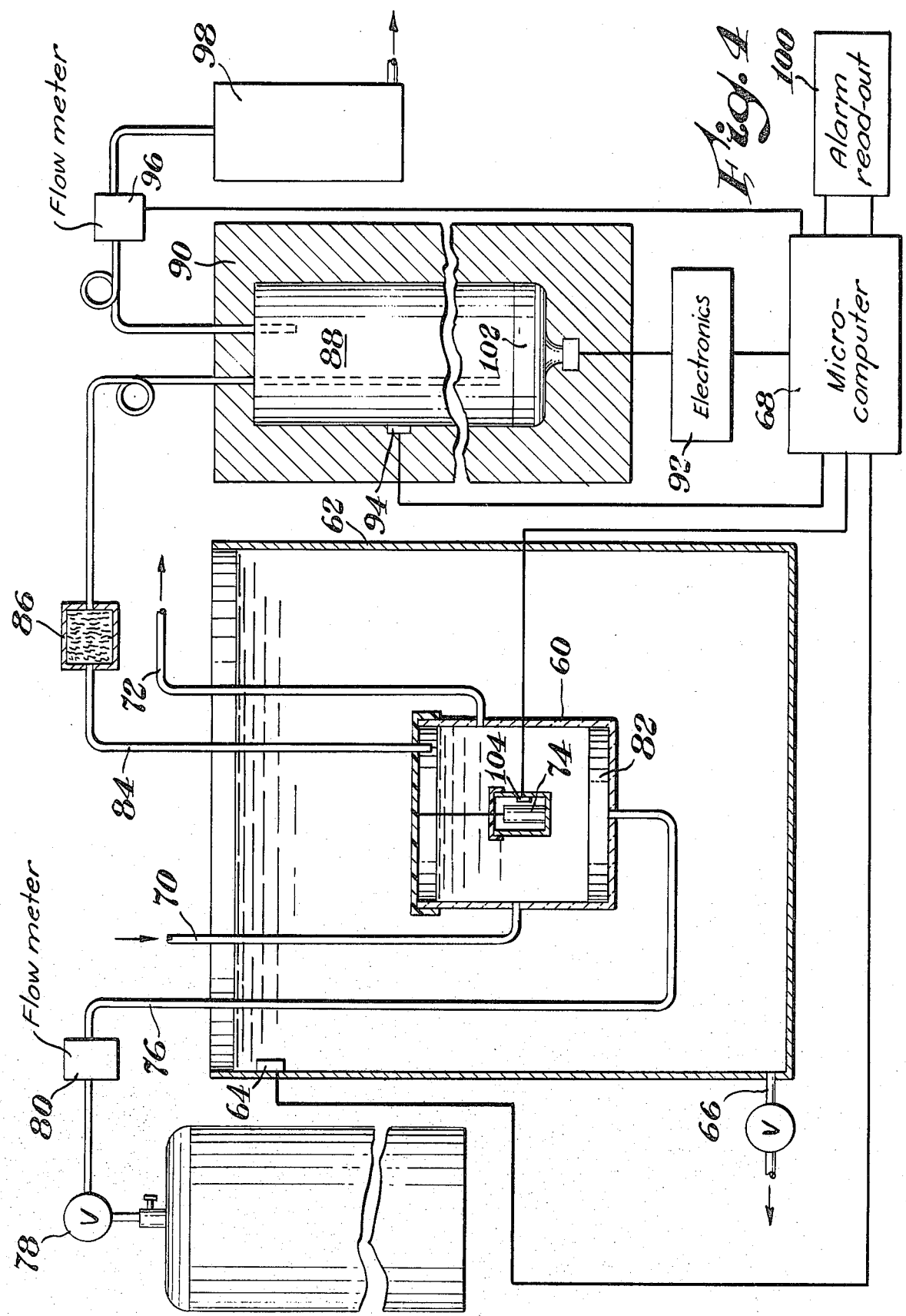
FIG. 4 is an elevational view of a modified apparatus constructed according to the invention and comprises apparatus designed for process stream control.

Analytical apparatus for batch sampling and analysis for total sodium is shown in FIGS. 1-3. The apparatus comprises an activation cell or chamber 10. A sparger 12 in the form of a glass frit is positioned within the activation cell, and communicates by way of conduit means 14 with a compressed gas source 16 controlled through such means as a pressure regulator valve 18 and flow meter 20. Sample is placed or introduced into the activation cell through a removable lid 22. A neutron flux emitter or activation source 24 in the form preferably of a stainless steel encapsulated $^{241}$Am/Be isotope is removably contained within a lidded glass container 26. Container 26 is suspended from lid 22 to be positioned at the geometric center of liquid sample contained within the activation cell. The area defined above the level of liquid sample is herein referred to as the headspace 28. Headspace 28 communicates by way of conduit communication means 30 with an activated carbon filter 32, and thereafter a radiation detector 34.

Detector 34, shown in FIG. 2, comprises a chamber or hollow shell, e.g. of cylindrical geometry, manufactured of a plastic scintillator 36. About the scintillator 36 is a layer of aluminized Mylar ® sheet 38, which is painted over with a black paint covering 40 (see FIG. 3). The radiation counting chamber comprises the internal volume of plastic scintillator 36 which receives the headspace gas mixture through an inlet lead 42 and expels the headspace gas through an outlet lead 44, each of the leads being looped at 46, 48, respectively, to provide an optical barrier.

Scintillated light produced in the plastic scintillator is processed by a photomultiplier tube 50, which is operated by a high voltage power supply 52. The photomultiplier tube converts the scintillator radiation to electrical voltage pulses of distinct energy, which pulses are fed through a pre-amplifier 54 and amplifier 56 to a multichannel analyzer 58. The multichannel analyzer processes the voltage pulses into a visible display such as the spectrum shown in FIG. 5, wherein the pulses are sorted according to energy.

FIG. 4 shows apparatus equivalent in certain aspects to the described batch analyzer but which includes modifications to produce an on-line process stream analyzer. The on-line analyzer comprises a flow through activation cell 60 which is immersed within a neutron shield comprising a shielding tank 62 filled, e.g., with a water/borax solution suitable for neutron absorption. Any soluble form of boron or soluble borate acceptable to form a neutron barrier or shield according to the known art may be used in tank 62. The shielding tank is preferably equipped with a level detector 64 and drain 66. The level detector is controlled by a microcomputer 68.

The activation cell is modified to receive and dispel a continuous liquid sample stream through inlet tube 70 and outlet tube 72. Outlet tube 72 leads to a waste disposal drain or container, or, depending on the toxicity and radioactive condition of the spent sample, the outlet tube may be connected to return sample to the process stream from which it was extracted. The activation cell is preferably equipped with a suspended form of $^{241}$Am/Be isotope 74 in the manner previously described, but modified to include a conductivity probe 104 monitored by microcomputer 68 to detect leakage of sample into the isotope container. Most desirably, metered sparging gas is brought into the shielding tank and activation cell through line 76 equipped with a pressure regulator 78 and flow meter 80. A glass frit sparger 82, preferably coextensive with the inner bottom of the activation cell, is used to produce a fine division of the incoming gas to obtain optimum sparging efficiency.

In the manner previously described, the headspace gas is withdrawn through an outlet conduit means 84 through an activated carbon filter 86 and ultimately to a plastic scintillator detector 88 which is encased within a background radiation shield comprising a lead shield 90. The detector 88 with photomultiplier tube 102 and associated electronic module 92 is a similar design to that of the batch apparatus, but desirably additionally includes a beta check source 94, preferably comprising encapsulated $^{90}$Sr isotope which intermittently communicates with the active wall of the scintillator through shutter means operated by microcomputer 68. For example, a lead shutter corresponding in design to model D1300SS available commercially from Blake Industries, Inc., Scotch Plains, New Jersey, may be suitably employed as the shutter means. The gas expelled from scintillator 88 is routed through a flow meter 96 which is preferably monitored by the microcomputer to assure proper operation, e.g. leak detection or other malfunctions as would be caused by increased or decreased gas flow through meter 96. The meter expels the gas ultimately to a baffled reservoir 98 which is designed to provide ample residence time such that $^{23}$Ne decay is complete before venting. A microcomputer suitable for the apparatus would comprise an Intel 80/20. The Intel 80/20 would preferably be interfaced with a module 92 representing the electronics described with respect to FIG. 2 to thus operate the apparatus on a continuous mode to provide instant readout and alarm monitoring. Deviations from normal operation would be desirably additionally indicated visually and audibly through an audio alarm module 100.

The operation of the batch and continuous stream monitor are, in principle, identical. Sample is individually loaded in the batch system, while either batch or continuous sample is fed to the flow cell. Residence time is sufficient for the extraction step to produce a detectable concentration of radioactive $^{23}$Ne mixed with sparging gas. The headspace gas mixture comprising predominantly sparging gas with a minute quantity of $^{23}$Ne, is filtered to remove any organic gas and/or sample liquid present to avoid detector contamination. The filtered gas is thereafter monitored for radiation count and expelled from the scintillator to the flow meter and ultimately baffled reservoir before being discharged from the system.

In respect to the on-line system, periodically the shutter means is opened by programming the microcomputer, thus allowing the detector to respond to the $^{90}$Sr source. The detector efficiency is thus monitored periodically to note any irregularities and possible malfunctions. Malfunctions as may be indicated by deviations from normal as indicated by level detector 64 or flow meter 96 are similarly responded to audibly and visually through alarm module 100.

The several example series below comprise data generated using the batch analyzer of FIGS. 1-3 using, more specifically, an activation cell comprising a glass container with a screw-on plastic lid modified with inlet and outlet glass tubes. The activation cell used in most of the experiments is 16 cm diameter and 22 cm high and holds approximately 4500 cc. Two other cells (2000 cc and 1000 cc) are used in the sample size experiment. Headspace is controlled at approximately 700 cc, 500 cc, and 400 cc for these experimental activation cells, respectively.

The source is sealed in a glass container approximately 4 cm diameter and 8 cm high. A glass frit 6 cm in diameter is used to disperse the sparging gas ($N_2$). The flow rate of the gas is controlled by a regulator and calibrated flow meter. The sparging gas is transferred from the activation cell to an activated charcoal filter and the detector through 30 feet of ¼ inch PVC tubing. The gas from the detector is vented through a fume hood. The activation cell is separated from the detector by four feet of water and four feet of concrete.

The detector specifically is a ½ inch plastic scintillator manufactured by Nuclear Enterprises, Inc., San Carlos, California. The scintillator is a right cylinder, O.D.-12.7 cm, I.D.-10.2 cm, height-30.5 cm. One end is solid and is coupled to the PMT. The other end has two holes 1.3 cm diameter for gas inlet and outlet ports or port means. The inlet lead is copper and extends through the inlet port to approximately 2 cm from the other end plate. The outlet lead extends through the outlet port to a position about 6 cm into the scintillator. This arrangement allows good mixing and permits the most active gas to be in the most efficient volume of the detector. The electronics used to process the signal include an Ortec 276 Photomultiplier base preamp, Ortec 471 Amplifier, Ortec 456 high voltage supply, D. S. Davidson 1056A multichannel analyzer.

EXAMPLE 1 (FLOW RATE)

Count rate is related to the flow rate of the sparging gas. As the flow rate increases, the sparging efficiency in removing $^{23}$Ne from the sample increases resulting in higher count rate. If the flow rate is too high, the residence time in the detector is reduced resulting in theoretically a lower count rate. This is confirmed by the data in Table I.

TABLE

| Count-Rate vs. Flow-Rate of $N_2$ | |
|---|---|
| Flow Rate (ml/min) | Count Rate |
| 60 | 318 |
| 150 | 8,114 |
| 300 | 31,855 |
| 580 | 62,344 |
| 910 | 79,640 |
| 1230 | 84,584 |
| 1580 | 84,796 |
| 1920 | 85,512 |
| 2600 | 82,983 |
| 3320 | 80,380 |
| 4610 | 67,877 |

EXAMPLE 2 (SAMPLE SIZE)

The size of the sample is additionally related to the count-rate because more sodium atoms are exposed to the neutron flux. This relationship is not expected to be linear because the distance the neutrons travel is greater for larger samples. This results in losses due to absorption and energy losses of the neutrons. Three sample sizes are evaluated for sample size effect. A 1000 cc cell does not allow a 2.0 L/m flow rate. Under the same conditions, a 4500 cc cell results in 13000 counts and a 2000 cc cell results in 9000 counts. The 1000 cc cell is substantially lower, but since the flow rate of 2.0 L/m is not attained, a quantitative value could not be obtained. The 4500 cc apparatus is selected for use in most of the experiments based on these results.

EXAMPLE 3 (MATRIX EFFECTS)

The applicable scope of the analysis should be relatively independent of the sample matrix so long as the sample is a liquid. Variations may be expected to occur because of differences in density, hydrogen density, and viscosity of the matrix, but the chemical state of the sodium should not affect the response. In a confirming experiment, a solution of 1% NaCl (0.39% Na) in water and 1% NaOH (0.57% Na) in isopropanol/methanol is run through the apparatus and the responses are compared. The response factor for the aqueous sample is $6015 \pm 200$ counts/% Na and $5073 \pm 200$ counts/% Na for the organic sample. The response factors are thus of the same magnitude. Although separate calibration curves would be necessary, the analysis is thus applicable with equally satisfactory results to either such matrix.

EXAMPLE 4 (SOURCE EFFECTS)

The response factor is calculated for a $^{241}$Am/Be source in the 4500 cc apparatus. The source is removed and the activation cell is placed in front of a Kaman A-711 14 MeV neutron generator. The neutron generator is operated at 160 KeV and 1.0 mA which is about 20 percent of the full power neutron output. A deionized water sample is run to establish a blank, and a 111 ppm NaCl solution is run to determine a response factor. A one minute delay loop is inserted in the transfer line between the activation cell and detector to remove $^{16}$N interference (see Example 5, below) produced from oxygen in the water. When the $^{241}$Am/Be source is replaced with the generator, the response factor increases from $1.25 \times 10^3$ counts/% NaCl to $1.25 \times 10^6$ counts/% NaCl. This could be increased still further by redesigning the activation cell to improve the geometry vis-a-vis the use of neutron generator. The detection limit using the current 4500 cc apparatus and the neutron generator is 1 ppm Na.

EXAMPLE 5 (INTERFERENCES)

Several elements theoretically could interfere. A short-lived radioactive gas must be generated by an interfering reaction to cause an interference in the analysis. Nuclear parameters for several possible interferences are listed in Table II.

TABLE II

Nuclear Parameters for Possible Interfering Reaction

| Element | Reaction | Neutron Energy Required | Product Half-Life | Energy (MeV) |
|---|---|---|---|---|
| Na | $^{23}$Na(n,p)$^{23}$Ne | 3.6 MeV | 37.5 s | 4.4,4.0 $\beta^-$ |
| Mg | $^{26}$Mg(n,$\alpha$)$^{23}$Ne | 5.4 MeV | 37.5 s | 4.4,4.0 $\beta^-$ |
| K | $^{41}$K(n,p)$^{41}$Ar | 1.7 MeV | 1.83 h | 1.2 $\beta^-$ |
| Ca | $^{44}$Ca(n,$\alpha$)$^{41}$Ar | 2.7 MeV | 1.83 h | 1.2 $\beta^-$ |
| Cl | $^{37}$Cl(n,$\gamma$)$^{38}$Cl | .025 eV | 37.3 m | 4.9 $\beta^-$ |
| Rb | $^{87}$Rb(n,p)$^{87}$Kr | 3.1 MeV | 76 m | 3.5,3.9 $\beta^-$ |
| Ba | $^{138}$Ba(n,$\alpha$)$^{135}$Xe | 3.8 MeV | 15.3 m | 0.9 $\beta^-$ |
| O | $^{16}$O(n,p)$^{16}$N | 9.6 MeV | 7.1 s | 4.3,10.4 $\beta^-$ |

As the data in Table II indicate interferences may occur from several elements. However, the half-lives of the resulting isotopes are long enough such that few disintegrations occur in the detector. The resulting response factors would thus be quite low. The $^{16}$O(n,p)$^{16}$N and $^{26}$MG(n,$\alpha$)$^{23}$Ne reactions require a neutron flux of significantly higher energy than the analytical reaction. The $^{241}$Am/Be source does not supply enough neutrons of sufficient energy to cause a significant interference from these reactions. Concentrated aqueous solutions of Cl, K, and Mg are run on the 4500 cc apparatus and no response is detected. The analysis is thus judged to be substantially free of any difficult known interferences.

EXAMPLE 6 (DETECTOR EFFICIENCY)

Detector efficiency is expected to decrease as the distance from the PMT increases. A $^{90}$Se source is used as the check source. Only a few points are taken because shielding due to tape on the scintillator interferes with the measurements. The results of the test are listed in Table III. While the trend is predicted, the magnitude of the losses is not judged large enough to necessarily justify a shorter scintillator design. It would be advantageous to make the diameter of the scintillator larger and add plastic scintillator baffles to increase sensitivity.

TABLE III

Detector Efficiency vs. Distance from Photomultiplier Tube

| Distance (cm) | Count |
|---|---|
| 10 | 5642 |
| 18 | 4015 |
| 25 | 3080 |
| End plate (30) | 971 |

EXAMPLE 7 (WINDOW SETTING)

Figure 5:
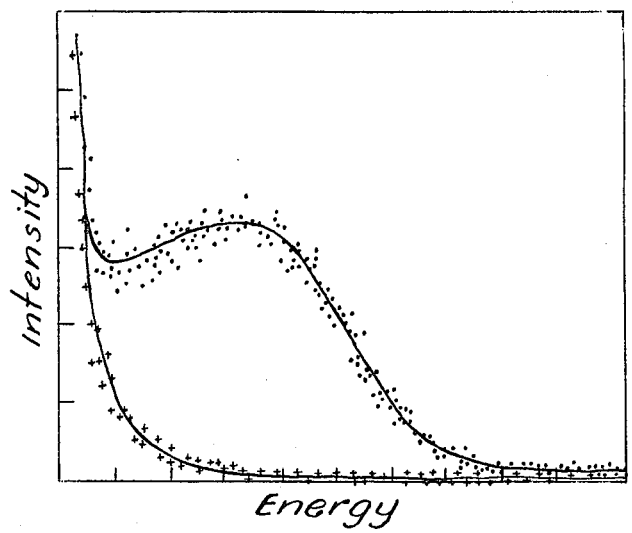
FIG. 5 is a typical spectrum of beta emission developed using the method and apparatus of the invention.

The $\beta^-$-ray spectrum of the $^{23}$Ne is collected on a multichannel analyzer. A spectrum of 10% NaCl solution and background is shown in FIG. 5. Note the broad distribution of counts for $^{23}$Ne. The window is determined by selecting the valley between the peak and background as the low energy limit and the point at which the peak reaches background at the high energy side as the high energy limit. As an alternate electronic arrangement, the described counting tabulation may be performed using a single channel analyzer and a counter timer in place of the described multichannel analyzer.

EXAMPLE 8 (CALIBRATION)

Figure 6:
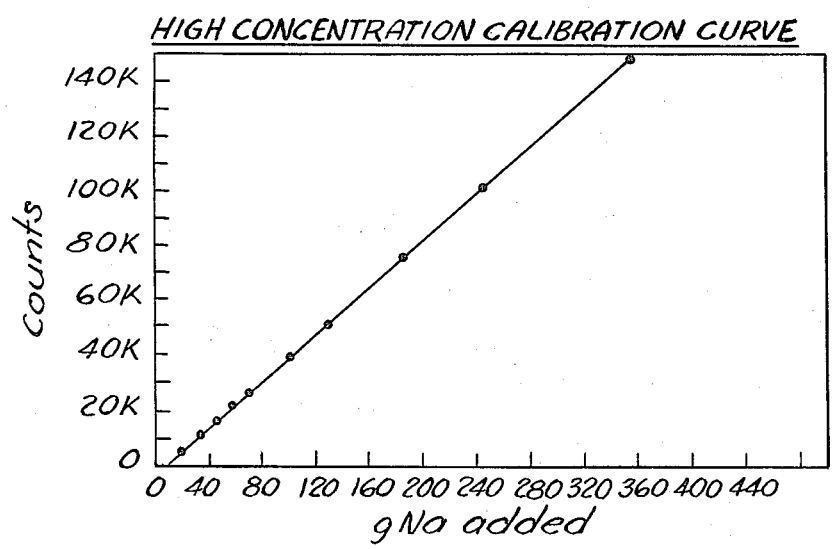
FIGS. 6 and 7 illustrate calibration curves developed using the method and apparatus hereof, for high and low concentrations of sodium, respectively.
Figure 7:
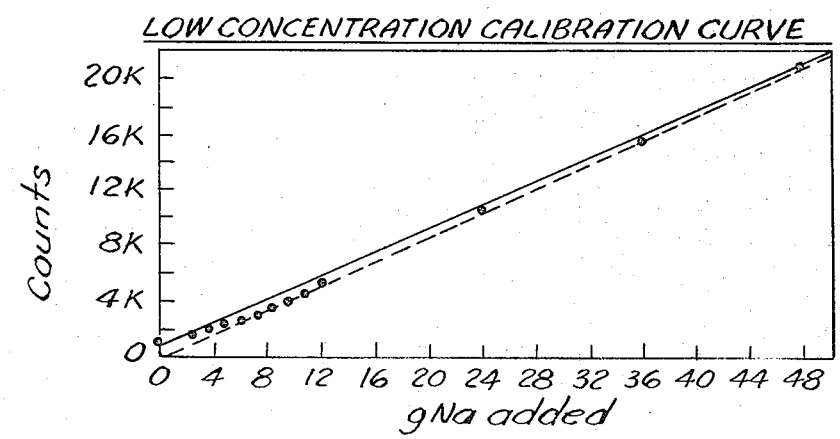

A calibration curve, which is generated for the 4500 cc apparatus using aqueous NaCl solutions, is shown in FIGS. 6 and 7. FIG. 6 shows the high concentration end of the curve. The response in FIG. 6 is linear in relation to the amount of NaCl in the container. FIG. 7 shows the low concentration range. The solid line is an extrapolation from the curve in FIG. 6. Note that the data indicate a negative deviation from the linear extrapolation. This is caused by the inefficient removal of $^{23}$Ne at low concentrations. As the NaCl concentration increases, the surface tension decreases allowing smaller bubbles of sparging gas to form. This apparently allows more efficient removal of $^{23}$Ne. If the surface tension of the sample is always constant, the deviation would be absent. If the deviation is a function of Na concentration as in this case, it can be corrected by applying a second order calibration curve. Accordingly, a constant volume sample can be used in this analysis as long as the density is constant or known because the method is sensitive to the total amount of Na present, not to the NA concentration as such.

What is claimed is:

1. Analytical method for determining total sodium which comprises exposing sodium containing liquid sample to a neutron flux effective to produce $^{23}$Ne radioactive gas activation product, sparging the liquid sample effective to evolve and separate from the sample a detectable concentration of $^{23}$Ne admixed with sparging gas, flow removing said evolved gas mixture to a space remote from the neutron flux emission, monitoring said removed gas mixture for radiation emission, and quantifying based on radiation count, total sodium of the analyzed sample.

2. The method of claim 1 using as a neutron flux emitter an activation source of about 3.6–14 MeV, average energy, and about 0.1–50 Ci.

3. The method of claim 1 using the step of immersing a radioactive isotope within the liquid sample to expose the sample to said neutron flux.

4. The method of claim 3 using $^{241}$Am/Be radioactive isotope.

5. The method of claim 4 using $^{241}$Am/Be isotope of about 0.5–14 Ci.

6. The method of claim 5 wherein principally beta emission of said gas mixture is monitored.

7. The method of claim 1 using the step of flow-through of the evolved gas mixture through a hollow plastic scintillator to monitor beta emission.

8. The method of claim 7 using the step of immersing a radioactive isotope within the liquid sample to expose the sample to said neutron flux.

9. The method of claim 8 wherein said immersed isotope is $^{241}$Am/Be.

10. Analytical apparatus for neutron activation analysis which comprises an activation cell, an activation source for producing a neutron flux within said activation cell, means to place sample within said activation cell, means to sparge said liquid sample, a headspace being defined for receiving sparging gas in admixture with gas sparged thereby which is evolved from the liquid sample, a radiation detector remote from said activation cell, means shielding the radiation detector from neutron flux emission and background radiation emission, communication means for routing flow of the headspace gas mixture to the radiation detector to detect radiation emission of said gas mixture.

11. The apparatus of claim 10 comprising as the activation source, $^{241}$Am/Be radioactive isotope within the activation cell.

12. The apparatus of claim 10 comprising, as the radiation detector, a plastic scintillator.

13. The apparatus of claim 10 comprising, as the radiation detector, a flow-through hollow chamber, said chamber comprising a plastic scintillator.

14. The apparatus of claim 13 comprising, as the activation source, $^{241}$Am/Be within the activation cell.

15. The apparatus of claim 10 comprising as the activation source, a neutron generator.

16. The apparatus of claim 10 comprising as the activation source, $^{241}$Am/Be radioactive isotope.

17. The apparatus of claim 16 wherein the isotope is disposed within the activation cell.

18. The apparatus of claim 17 comprising as the radiation detector, a beta detector.

19. The apparatus of claim 18 wherein said beta detector comprises a plastic scintillator.

20. The apparatus of claim 18 comprising as the radiation detector, a flow-through hollow chamber, said chamber comprising a plastic scintillator.

* * * * *

UNITED STATES PATENT AND TRADEMARK OFFICE
CERTIFICATE OF CORRECTION

PATENT NO. : 4,293,379
DATED : October 6, 1981
INVENTOR(S) : Kerry J. Kelly et al.

It is certified that error appears in the above-identified patent and that said Letters Patent are hereby corrected as shown below:

Col. 2, line 13, delete "solved" and insert --evolved--.

Col. 8, line 68, delete "NA" and insert --Na--.

Col. 9, line 2 of Claim 5, delete "0.5-14" and insert --0.5-15--.

Signed and Sealed this

Twelfth Day of January 1982

[SEAL]

Attest:

Attesting Officer

GERALD J. MOSSINGHOFF

Commissioner of Patents and Trademarks